United States Patent [19]

Jenkins, deceased

[11] Patent Number: Plant 5,472

[45] Date of Patent: May 21, 1985

[54] RED DELICIOUS APPLE TREE—JENRED CULTIVAR

[75] Inventor: Philip J. Jenkins, deceased, late of Yakima, Wash., by Zona G. Jenkins, legal representative

[73] Assignee: Stark Brothers Nurseries & Orchards Company, Louisiana, Mo.

[21] Appl. No.: 494,553

[22] Filed: May 13, 1983

[51] Int. Cl.[3] ..... A01H 5/03

[52] U.S. Cl. ..... Plt./35

[58] Field of Search ..... Plt./35

*Primary Examiner*—Robert E. Bagwill

*Attorney, Agent, or Firm*—Burns, Doane, Swecker & Mathis

[57] ABSTRACT

A new and distinct spur-type Red Delicious apple variety is provided which originated as a limb mutation of the apple tree of U.S. Plant Pat. No. 2,816. The fruit of the new variety is conic shaped and highly attractive since at maturity it is fully covered with conspicuous dark red stripes over a bright red ground color. Unlike fruit formed on the parent, the fruit of the new variety colors approximately 15 days earlier, and colors more fully in years when environmental conditions do not favour the coloring of Red Delicious apples.

1 Drawing Figure

SUMMARY OF THE INVENTION

The new variety was discovered by its originator in July 1979 as a bud or limb mutation on a Red Delicious apple tree of U.S. Plant Pat. No. 2,816. Such parent variety is being marketed under the Oregon Spur trademark. The limb mutation was found in an orchard on the Royal Slope of the Columbia Basin near Royal City, Grant County, Wash. More specifically, the limb mutation was found in an orchard owned by Norman Byrd at Block 80, Section 118. This general area is noted for late apple coloring and maturity and is at least one week behind the fruit district at Yakima, Wash. in this respect.

The originator was serving as an orchard consultant at the time of the discovery of the new variety and while carefully observing the entire orchard was attracted to a single limb. The fruit of this limb exhibited attractive red stripes at a time when other fruits in the orchard were totally green. The originator marked the limb with colored ribbons and continued to observe it throughout that season and into the next season.

The fruit was found to be of uniform size and to exhibit a conic (i.e. typey) shape. The fruit when fully mature has a bright red ground or under color and is marked by an overlay of conspicuous dark red stripes. Also, the fruit colors approximately 15 days earlier than the parent variety growing in the same orchard. In 1979 when environmental conditions favored the coloring of Red Delicious apples the fruit when mature resembled closely that of the parent variety. However, in 1980 when environmental conditions were not as favorable for fruit coloring, the new variety stood out at maturity as having much more red coloration than its patent coupled with the concomitant absence of green coloration. Also, the fruit of the new variety has considerable more red coloration than that of the Campbell cultivar of U.S. Plant Pat. No. 3,578 which was growing in the same orchard and which is being marketed under the Redchief trademark. For instance, the Campbell cultivar yielded mature apples which included substantial green coloration under the same growing conditions.

Asexual propagation on behalf of the originator at Louisiana, Mo. beginning in September 1979 has demonstrated that the unique combination of characteristics of the new variety comes true to form and is established and transmitted through succeeding propagations. All specimens described herein were grown on the parent tree located near Royal City, Grant County, Wash.

The new variety has been named the Jenred cultivar in honor of its originator, and is being marketed by the Stark Brothers Nurseries & Orchards Company under the Starkspur and Ultrastripe trademarks.

BRIEF DESCRIPTION OF THE PHOTOGRAPH

The accompanying photograph shows typical specimens of the fruit and foliage of the new variety in color as nearly true as it is reasonably possible to make the same in a color illustration of this character.

DETAILED DESCRIPTION OF THE NEW VARIETY

The following is a detailed description of the new variety where color terminology is to be accorded its ordinary dictionary significance except where otherwise indicated. The specimen described was grown near Royal City, Grant County, Wash.

Representative dates of first and last pickings were Sept. 9, 1981 and Sept. 16, 1981.

Tree: Medium small; medium vigorous; upright; dense; rapid growing; very productive; regular bearing.

*Trunk.*—Medium stocky; medium smooth.

*Branches.*—Medium thick; medium smooth; little branching; many spurs on limbs; brown — Maroon — plate 1 color No. 3 tone m of Ridgeway Color Standards and Nomenclature. Lenticels — medium few; medium small.

*Leaves.*—Medium large; medium wide; medium long; ovate; taper pointed; thick; medium dark green; Dark Sulfate Green Plate XIX Color No. 39′ tone i of Ridgeway Color Standards and Nomenclature; rugose. Length — approximately $3\frac{5}{8}$ inch. Width — approximately 2 3/16 inch. Margin — coarsely serrate. Petiole — medium long (approximately 1 inch); thick.

Flowers: Medium early; large; white — edges tinged with Carmine — plate 21/3 p 21 Vol. 1 of the Horticultural Color Guide.

Fruit:

*Maturity when described.*—Hard ripe — Sept. 9, 1981.

*Size.*—Uniform. Axial diameter — approximately $3\frac{1}{4}$ to $3\frac{1}{2}$ inches. Transverse in suture planes — approximately 3 inches.

*Form.*—Conical; ribbed.

*Cavity.*—Symmetrical; rounded toward apex; acute; undulate; pubescent toward apex. Depth — approximately $\frac{5}{8}$ inch. Breadth — approximately $1\frac{1}{8}$ inch. Markings — light russet.

*Basin.*—Symmetrical; abrupt at base; flaring; wide; furrowed; glabrous. Depth — approximately $\frac{5}{8}$ inch. Breadth — approximately $1\frac{1}{8}$ inch. Markings — none.

*Stem.*—Clubbed; stout; pubescent. Length — approximately $\frac{7}{8}$ inch. Breadth — approximately 3/32 inch. Markings — none.

*Calyx.*—Closed; segment persistent; broadly lanceolate; acute. Length — approximately 5/16 inch; approximate at base; prostrate; reflexed from base at apex; connivent. Outer-surface — pubescent. Inter-surface — pubescent.

*Eye.*—Small; partially closed.

*Skin.*—Thick; tough; smooth; glossy; waxed. Dots — obscure; many; small; depressed; circular. Color of dots — white. Distribution of dots — all over; most numerous toward basin. Ground color — Scarlet, Plate I, Color No. 5 of Ridgeway Color Standards and Nomenclature. Color of markings — striped; self colored; bright; Nopal Red Plate 1. Color No. 3 — tone i of Ridgeway Color Standards and Nomenclature. Bloom — wanting. Scarfskin — wanting. General color effect — bright red with dark red stripes.

*Flesh.*—Juicy. Color — satiny white with greenish tint. Texture — firm; fine; crisp. Flavor — mild sweet; quality good.

*Core.*—Medium. Bundle area — medium small; oblate symmetrical; acute at base. Bundle color — light green; inconspicuous, in one whorl. Core lines — clasping; in cross-section indistinct. Carpellary area — indistinct; small. Calyx tube — glabrous toward base; funnel-form. Stem of funnel — long. Depth of tube to shoulder — approximately $\frac{3}{8}$ inch. Entire depth — approximately 9/16 inch. Styles — present; united toward base; pubescent toward base. Stamens — one distinct whorl; median. Seed cells — axile; closed. Cell walls — approximate; thin; tough. Length — approximately $\frac{5}{8}$ inch. Breadth — approximately 5/16 inch. Longitudinal section — broadly ovate. Surface — smooth. Cross-section — narrow.

*Seeds.*—Number perfect — 7; number imperfect — 1. Number in one cell — 2. Length — approximately 5/16 inch. Breadth — approximately 3/16 inch. Form — acute. Color — brown.

Use: Market — dessert.

Keeping quality: Good.

Number of days in ordinary storage: Approximately 120 days.

Resistance to insects: Medium.

Resistance to diseases: Medium.

I claim:

1. A new and distinct variety of spur-type Red Delicious apple tree substantially as illustrated and described, characterized by the ability to form attractive conic shaped fruit having conspicuous dark red stripes over a bright red ground color and a general similarity to its parent described in U.S. Plant Pat. No. 2,816, but being distinct therefrom by the ability of its fruit (a) to color approximately 15 days earlier, and (b) to color more completely each year in spite of environmental conditions which do not favor the fruit coloring of Red Delicious apples.

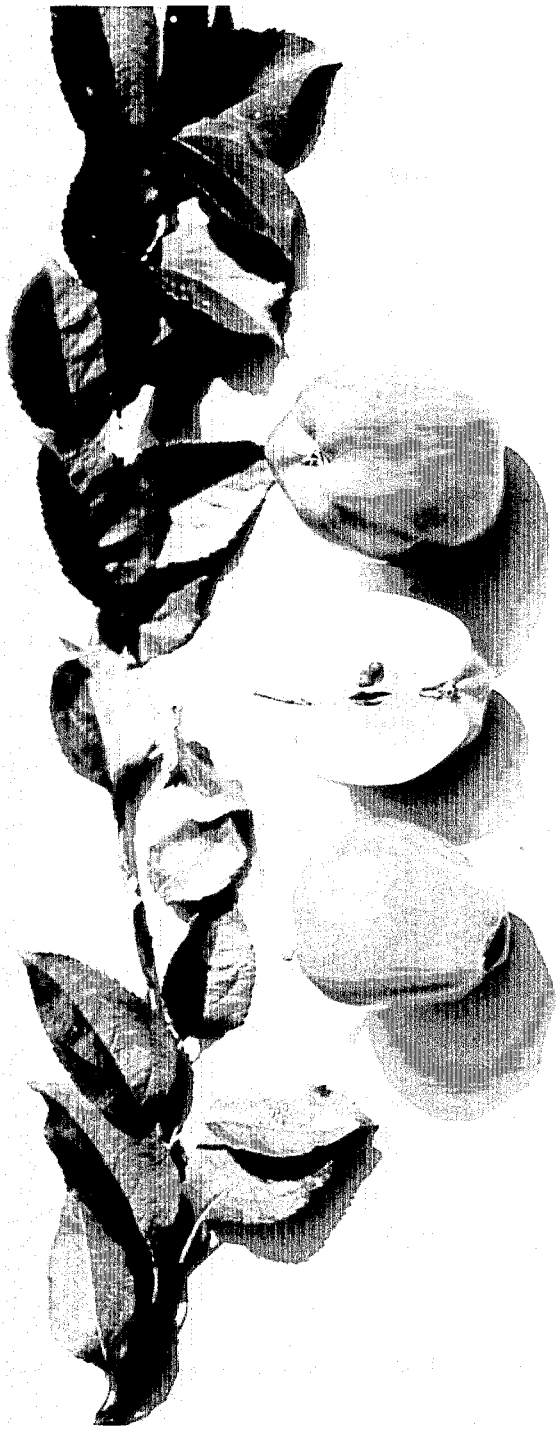

* * * * *